US00PP16854P2

(12) United States Plant Patent
Boeder

(10) Patent No.: US PP16,854 P2
(45) Date of Patent: Jul. 18, 2006

(54) ***CHRYSANTHEMUM* PLANT NAMED 'CESHAKIRA WHITE'**

(50) Latin Name: *Chrysanthemum morifolium*
Varietal Denomination: Ceshakira White

(75) Inventor: Mark Roland Boeder, The Hague (NL)

(73) Assignee: Chrysanthemum Breeders Association N.V., Aalsmeer (NL)

( * ) Notice: Subject to any disclaimer, the term of this patent is extended or adjusted under 35 U.S.C. 154(b) by 0 days.

(21) Appl. No.: 11/128,370

(22) Filed: May 13, 2005

(51) Int. Cl.
*A01H 5/00* (2006.01)

(52) U.S. Cl. ..... Plt./288
(58) Field of Classification Search ..... Plt./288
See application file for complete search history.

*Primary Examiner*—Kent Bell
*Assistant Examiner*—Annette H Para
(74) *Attorney, Agent, or Firm*—Steptoe & Johnson LLP

(57) ABSTRACT

A *Chrysanthemum* plant named 'Ceshakira White' characterized by its large sized spider type inflorescences with white ray-florets and a green disc, with a response time of 50 days, and which can be grown as a spraymum as well as a disbud mum.

3 Drawing Sheets

BACKGROUND OF THE INVENTION

'Ceshakira White' is a product of a breeding-program which had the objective of creating new *chrysanthemum* cultivars with a spider type flower, a 7 week response and a medium plant height (90 cm). The new plant of the present invention comprises a new and distinct cultivar of *Chrysanthemum* plant. 'Ceshakira White' is a seedling from a cross in a breeding program maintained under the control of inventor. The female parent is # 16104—unpatented—, an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout, The Netherlands in 2002. The first act of asexual reproduction of 'Ceshakira White' was accomplished when vegetative cuttings were taken from the initial selection in 2002 and propagated further in a controlled environment in Rijsenhout, The Netherlands.

SUMMARY OF THE INVENTION

The present invention is a new and distinct variety of *chrysanthemum* bearing large sized double-type spider inflorescences with white ray-florets and a green disc; this spraymum variety can also be grown as a disbud.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
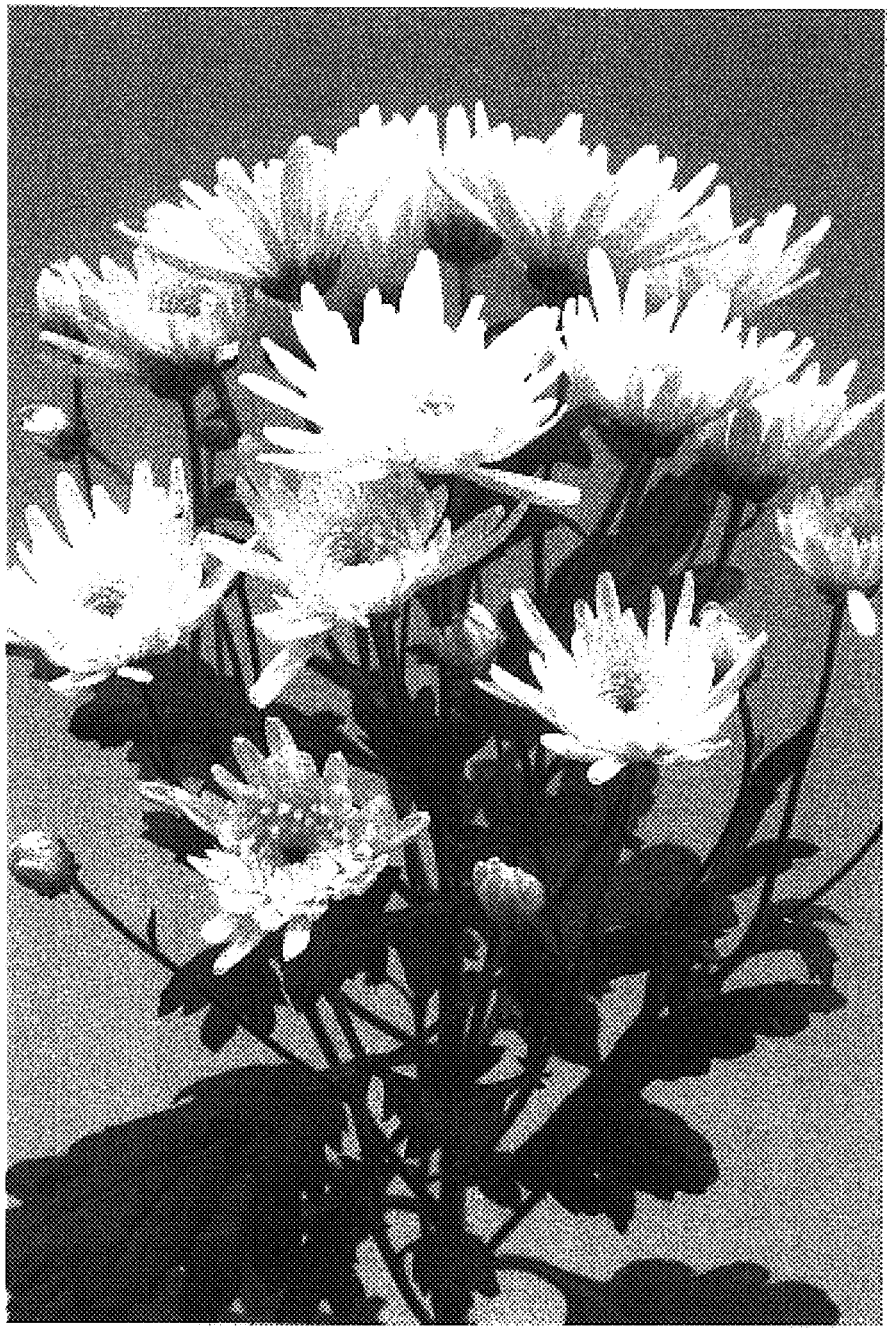
FIG. 1 shows a plant of the cultivar in full bloom.
Figure 2:
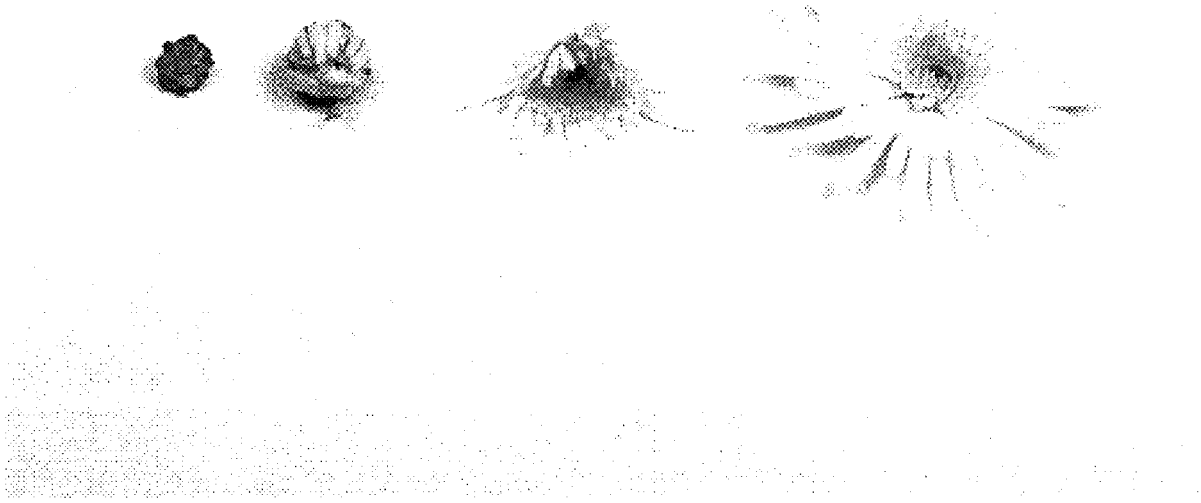
FIG. 2 shows the various stages of blooms of the new cultivar.
Figure 3:
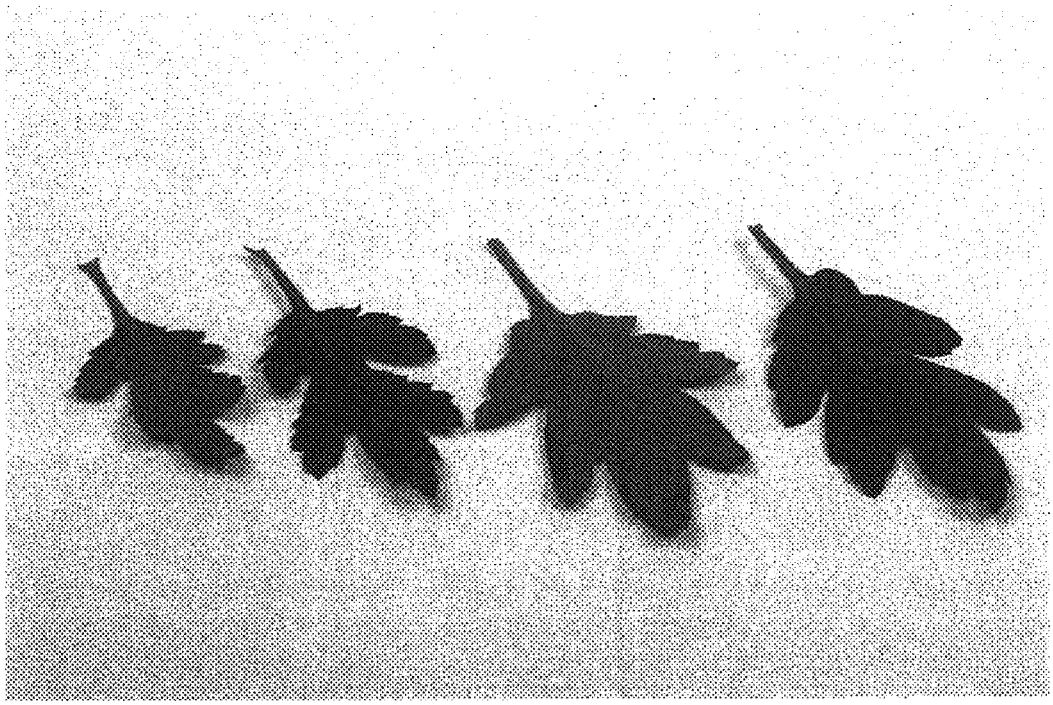
FIG. 3 shows the foliage of the new cultivar.

This new variety of *chrysanthemum* is of the botanical classification *Chrysanthemum morifolium*. The observations and measurements were gathered from plants grown in April/May in a greenhouse in Rijsenhout, The Netherlands in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 50 days. After the long day period to flowering growth retardants were applied 2 to 3 times in an average dose of 2.5 gram/liter water. The plants were observed (directly) during the flowering of this crop. This variety is sensitive to infestation by white rust, thrips and leaf miner. This new variety produces large sized spider inflorescences with white ray-florets and a green disc, flowering on the plant for 1 week. This new variety of *chrysanthemum* has been found to retain its distinctive characteristics throughout successive propagations, however the phenotype may vary significantly with variations in environment such as light intensity and temperature. To show the phenotype as described 'Ceshakira White' can be under greenhouse conditions in The Netherlands. With assimilation light (minimum level 2500 lux) it can be planted year round under greenhouse conditions.

From the cultivars known to inventor the most similar existing cultivars in comparison to 'Ceshakira White' is 'Delianne' non patented and 'Anastasia' (U.S. Plant Pat. No. 13,550). When 'Delianne', 'Anastasia' and 'Ceshakira White' are being compared the following differences and similarities are noticed: 'Delianne', 'Anastasia' and 'Ceshakira White' all have spider type white inflorescences. The differences of 'Delianne', 'Anastasia' and 'Ceshakira White' are (1) number of inflorescences per stem. 'Ceshakira White' produces a higher number of blooms per stem than 'Delianne' or 'Anastasia'. (2) visibility of disc florets. In mature flowers, the presence of disc florets is more conspicuous in 'Ceshakira White' than in 'Delianne' and 'Anastasia'. (3) Width of ray-florets. The width of ray florets of 'Anastasia' is smaller than that of 'Delianne' and 'Ceshakira White'.

The following is a description of the plant and characteristics that distinguish 'Ceshakira White' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of variety 'Ceshakira White' | |
|---|---|
| Bud | |
| Size | Medium, cross-section 1.2 cm height 0.8 cm |
| Outside color | Yellow-green 145 D with center of Green 143 A |
| Phyllaries | 2 rows, length 7 mm, width 3 mm |
| Phyllaries among disc-florets | Not present |
| Phyllaries color | Green 138 B |
| Inflorescence | |
| Type | Double |
| Height | 2 cm |
| Size | Large |
| Fully expanded | 7 cm (spraymum); 11 cm (disbud) |
| Number of inflorescences per stem | Average of 15 |
| Performance on the plant | 1 week |
| Seeds (if crossed) | Produced in small quantities, oval shaped, grey-brown 199 A, 2 mm in length. |
| Fragrance | Typical *chrysanthemum,* slight |
| Peduncle length | Near the top 6 cm, near the middle 10 cm, near the bottom 20 cm |
| Peduncle color | Green 143 A |
| Color | |
| Center of the flower (disc-florets) | Immature Green 143 A<br>Mature Green 143 A to Yellow-green 151 A |
| Color of the ray-florets | Upper surface Yellow-green 150 C (inner row) and White 155 D (outer row)<br>Lower surface Yellow-green 150 C (inner row) and White 155 D (outer row) |
| Tonality from Distance | A spray mum with white flowers and a green disc |
| Color of the upper surface of the ray-florets after aging of the plant | White 155 D |
| Ray florets | |
| Texture | Upper and under side smooth |
| Number | 220–230 |
| Cross section | Fused into tube |
| Longitudinal axis of majority | Incurving (inner row); straight (outer row) |
| Length of corolla tube | 1.5 cm (inner row) to 4.2 cm (outer row) |
| Ray-floret margin | Entire |
| Ray-floret length | 1.5 cm (inner row) to 4.3 cm (outer row) |
| Ray-floret width | 0.3–0.8 cm |
| Ratio length/width | 5 |
| Shape of tip | Quilled and occasionally spatulate |
| Disc florets | |
| Disc diameter | 1 cm |
| Distribution of disc florets | Few, only visible at mature stage of flowering |
| Shape | Tubular |
| Color | Yellow 11 D |
| Receptacle shape | Conical raised |
| Reproductive Organs | |
| Stamen | Present in disc florets only |
| Stamen color | Yellow-green 144 A |
| Pollen | Produced in small quantity |

TABLE 1-continued

| Botanical Description of variety 'Ceshakira White' | |
|---|---|
| Pollen color | Yellow 7 A |
| Styles | Present in both ray and disc florets |
| Style color | Yellow 13 A |
| Style Length | 4 mm |
| Stigma color | Yellow-green 145 D |
| Stigma Width | 1 mm |
| Ovaries | Enclosed in perianth |
| Plant | |
| Form | A spray mum meant for erect culture; also grown as disbud |
| Growth habit | Upright |
| Growth rate | Vigorous |
| Height | 90 cm |
| Width | 27 cm |
| Internode length | 2–3 cm |
| Spray formation | Corymbiform |
| Stem Color | Green 138 A–139 A |
| Stem Strength | Strong |
| Stem Brittleness | Not brittle |
| Stem Anthocyanin coloration | Absent |
| Flowering Response (photo-periodic controlled crop, not natural season) | 48–50 days in summer to 58 days in winter |
| Foliage | |
| Color immature stage | Upper side Green 143 A<br>Under side Green 138 A |
| Color mature stage | Upper side Yellow-green 147 A<br>Under side Green 138 A |
| Color midvein mature leaf | Upper side Yellow-green 147 D<br>Under side Yellow-green 148 D |
| Size | Large; length 13 cm, width 7 cm |
| Quantity (number per single stem) | 32 |
| Shape | Elliptic |
| Texture upper side | Fleshy and glabrous |
| Texture under side | Pubescent |
| Venation arrangement | Palmate |
| Shape of the margin | Serrate |
| Shape of Base of Sinus Between Lateral Lobes | Rounded |
| Margin of Sinus Between Lateral Lobes | Diverging |
| Shape of Base | Obtuse to asymmetric |
| Apex | Mucronulate |
| Petiole Length | 2–3 cm |
| Petiole Color | Yellow-green 147 D |

TABLE 2

| Differences with comparison varieties | | | |
|---|---|---|---|
| | 'Ceshakira White' | 'Delianne' | 'Anastasia' |
| Number of inflorescences | 15 | 12 | 12 |
| Visibility disc florets in mature flowers | visible | inconspicuous | inconspicuous |
| Width ray florets | More broad | More broad | Small |

I claim:

1. A new and distinct variety of *chrysanthemum* plant as described and illustrated.

* * * * *